United States Patent [19]

Skotnicki et al.

[11] Patent Number: 4,728,733
[45] Date of Patent: Mar. 1, 1988

[54] C-3' THIADIAZINYL CEPHALOSPORIN ANALOGS

[75] Inventors: Jerauld S. Skotnicki, Chadds Ford; Donald P. Strike, St. Davids, both of Pa.

[73] Assignee: American Home Products Corporation, New York, N.Y.

[21] Appl. No.: 801,460

[22] Filed: Nov. 25, 1985

[51] Int. Cl.$^4$ .................. C07D 501/36; A61K 31/545
[52] U.S. Cl. ...................................................... 540/227
[58] Field of Search ......................................... 540/227

[56] References Cited

U.S. PATENT DOCUMENTS 4,614,819  9/1986  Nagai et al. .................... 540/227 X

OTHER PUBLICATIONS

Skotnicki et al., Chem. Abstracts 105 (1986) entry 226119u.
Horrii et al., Chem. Abstracts 90 (19) entry 168628t.

Primary Examiner—Donald G. Daus
Assistant Examiner—William A. Teoli, Jr.
Attorney, Agent, or Firm—George Tarnowski

[57] ABSTRACT

There are disclosed novel antibacterial compounds having the formula wherein
R is hydrogen, lower alkyl, lower alkenyl, lower alkynyl, cyclo lower alkyl, aryl of 6–12 carbon atoms, all the said foregoing groups being optionally substituted with carboxy, lower alkoxycarbonyl, phenoxycarbonyl, amino, mono- or di-lower alkyl substituted amino, hydroxy, lower alkoxy, phenoxy, carbamoyl, lower alkyl carbonyl, benzoyl, cyano, nitro, formamido, lower alkanoylamino or benzamido;
$R^1$ is hydrogen, lower alkyl or an alkali metal cation;
A is $R^2$ and $R^3$ are each individually hydrogen, lower alkyl, carboxy, lower alkoxycarbonyl, cyano, nitro, trifluoromethyl, phenyl or naphthyl; or $R^2$ and $R^3$ taken together represent or a 5- or 6- membered unsaturated aza-, diaza-, triaza-, tetraza-, thia-, thiaza-, oxathia-, oxathiaza-, oxa-, dioxa-, oxaza- or oxadiazacyclic moiety; and the dotted line denotes an optional double bond; and
$R^4$ is hydrogen, lower alkyl, phenyl or naphthyl.

5 Claims, No Drawings

C-3' THIADIAZINYL CEPHALOSPORIN ANALOGS

The present invention is directed to C-3'-substituted cephalosporin derivatives having antibacterial activity. The compounds of the invention have the formula

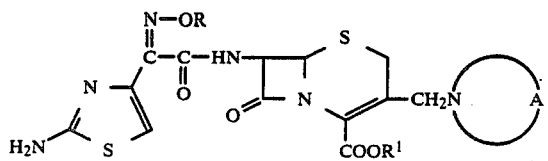

wherein
R is hydrogen, lower alkyl, lower alkenyl, lower alkynyl, cyclo lower alkyl, aryl of 6-12 carbon atoms, all the said foregoing groups being optionally substituted with carboxy, lower alkoxycarbonyl, phenoxycarbonyl, amino, mono- or di-lower alkyl substituted amino, hydroxy, lower alkoxy, phenoxy, carbamoyl, lower alkyl carbonyl, benzoyl, cyano, nitro, formamido, lower alkanoylamino or benzamido;
$R^1$ is hydrogen, lower alkyl or an alkali metal cation;
A is

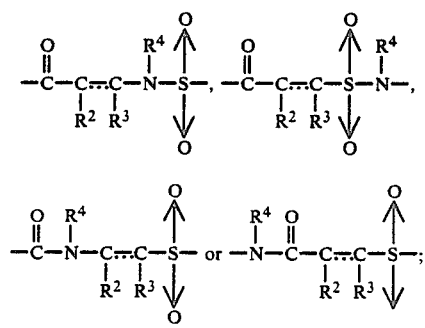

$R^2$ and $R^3$ are each individually hydrogen, lower alkyl, carboxy, lower alkoxycarbonyl, cyano, nitro, trifluoromethyl, phenyl or naphthyl; or $R^2$ and $R^3$ taken together represent

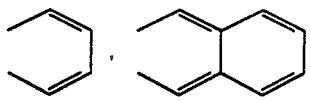

or a 5- or 6-membered unsaturated aza-, diaza-, triaza-, tetraza-, thia-, thiaza-, oxathia-, oxathiaza-, oxa-, dioxa-, oxaza- or oxadiazacyclic moiety; and the dotted line denotes an optional double bond; and $R^4$ is hydrogen, lower alkyl, phenyl or naphthyl.

The terms "lower alkyl" and "lower alkoxy" refer to unbranched or branched moieties having 1-6 carbon atoms in the carbon chain. "Lower alkanoyl" refers to moieties having 1-6 carbon atoms in a carbon chain attached to a carbonyl group. The terms, "lower alkenyl" and "lower alkynyl" refer to unbranched or branched moieties of the requisite degree of unsaturation having 2-6 carbon atoms in the carbon chain. The term "alkali metal cation" refers to $Na^+$ and $K^+$.

When $R^2$ and $R^3$ denote a 5- or 6-membered unsaturated aza-, diaza-, triaza-, tetraza-, thia-, thiaza-, oxathia-, oxathiaza-, oxa-, dioxa-, oxaza- or oxadiazacyclic moiety, this refers to but is not limited to moieties which can be a pyrrole, imidazole, triazole, tetrazole, pyridine, pyrimidine, pyrazine, pyridazine, triazine, tetrazine, thiazole, isothiazole, thiazine, oxathiole, oxathiazine, furan, pyran, dioxin, oxazole, oxazine, isoxazine, oxadiazole, oxadiazine and the like.

The compounds of the invention can be prepared by reacting a suitably protected cephalosporin derivative with a reactive species of the desired substituent A. The following reaction scheme, in which A is a thiadiazinone 1,1-dioxide, is representative of the preparative scheme in question:

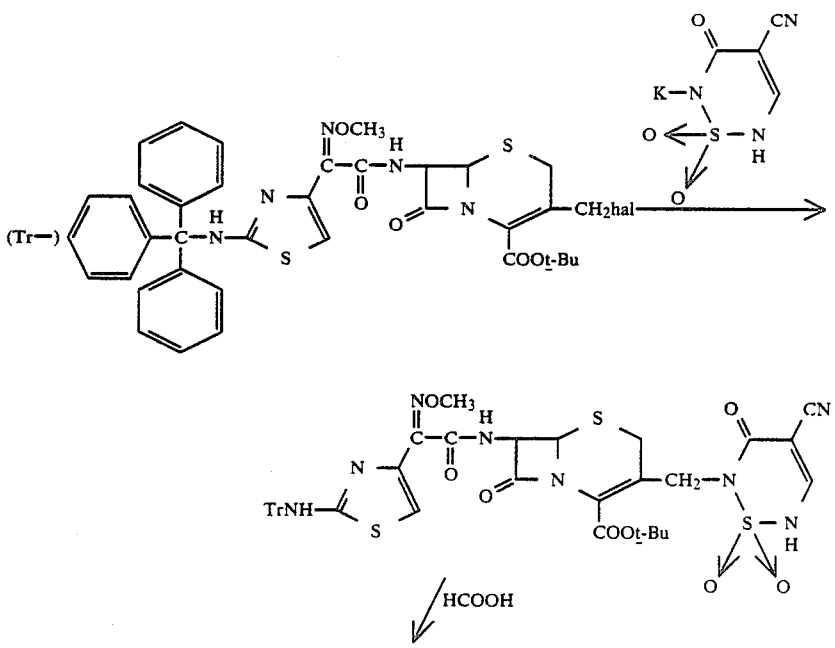

-continued

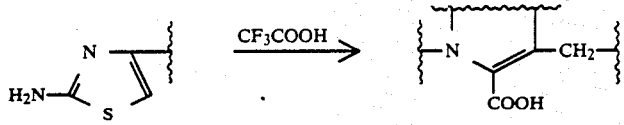

wherein hal refers to iodo, bromo or chloro. The initial reactive cephalosporin derivative has a suitably protected carboxyl group at the C-2' position and the amino group on the thiazole ring is also suitably protected. The protecting groups used include any readily displaceable groups known in the art for protecting primary amines and carboxylic acid groups. The exemplified protecting groups are triphenylmethyl (Tr) and t-butyl, respectively, and these groups are preferred. In the above scheme, the triphenylmethyl group is displaced with formic acid leaving a primary amine group on the thiazole ring, while in the last step the t-butyl group is displaced with trifluoroacetic acid, giving a carboxylic acid group in the cephalosporin C-2' position.

The starting cephalosporin derivative having the formula

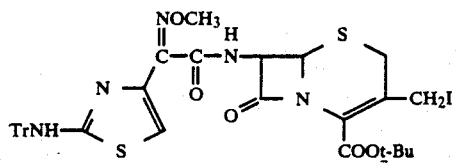

can be prepared according to the method described in Bonjouklian and Phillips, Tetrahedron Letters, 22, 3915 (1981). The A substituent-containing moieties are well-known in the art and are either commercially available or can be prepared by conventional methods, for example, such as those described in Goya and Stud, J. Heterocyclic Chem., 15, 253 (1978) and Cohen and Klarberg, J. Am. Chem. Soc., 84, 1994 (1962). The R moieties are known in the art (see e.g. U.S. Pat. No. 4,420,477).

The compounds of the invention are antibacterial agents effective against a variety of pathogenic Gram-positive and Gram-negative bacterial organisms, including penicillin-resistant Staphylococcus. Thus, the antibacterial compounds of the invention are useful in the therapeutic treatment of bacterial infections in poultry and animals, including man, as well as being useful as nutritional supplements in animal feeds. The compounds of the invention are particularly active against the Gram negative bacteria and exhibit β-lactamase stability.

Because of their antibacterial properties, the compounds of the invention can be formulated into therapeutically valuable compositions comprising compounds of the invention and pharmacologically acceptable carriers. The latter term contemplates usual and customary substances employed to formulate solid, oral unit dosages for pharmacological purposes. The term also includes those substances employed to formulate either in unit dose or multidose form, oral and injectable suspensions and solutions, either directly or for reconstitution before administration.

To formulate dosages for administration according to this invention the compounds of the invention can be compounded into oral dosage forms such as tablets, capsules and the like. This is done by combining the compounds with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter, and the like. Diluents, flavoring agents, solubilizers, lubricants, suspending agents, binder, tablet-disintegrating agents and the like may be employed. The active ingredient may be encapsulated with or without other carriers. In all cases, the proportion of active ingredients in said compositions both solid and liquid will be at least sufficient to impart antibacterial activity thereto on oral administration.

The compounds may also be injected parenterally, in which case they are used in the form of a sterile solution containing other solutes, for example, enough saline or glucose to make the solution isotonic. The compounds may also be used topically and for this purpose they may be formulated in the form of dusting powders, solutions, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter, the dosage is increased until the optimum effect under the circumstances is reached. In general, the compounds of the invention are most desirably administered at a concentration level that will generally afford effective results without causing any harmful or deleterious side effects.

The antibacterial activity of the compounds of the invention may be demonstrated by a standard pharmacological procedure which is described fully following the below presented examples directed to the preparation of the compounds useful in the invention.

PREPARATION OF STARTING CEPHALOSPORIN INTERMEDIATE (6R,7R)-3-(Iodomethyl)-7-[[(Z)-(methoxyimino)[4-[(triphenylmethyl)amino]-2-thiazolyl]acetyl]amino]-8-oxo-5-thia-1-azabicyclo[4.2.0]-oct-2-ene-2-carboxylic acid 1,1-dimethylethyl ester To a solution of 8.4 g (0.0111 mol) of (6R,7R)-3-acetoxymethyl-7-[[(Z)methoxyimino)[4-[(triphenylmethyl)amino]-2-thiazolyl]acetyl]amino]-8-oxo-5-thia-1-azabicyclo[4.2.0]oct-2-ene-2-carboxylic acid 1,1-dimethylethyl ester and 100 ml of $CH_2Cl_2$ at ambient temperature under a nitrogen atmosphere is added dropwise 3.35 ml (4.71 g/0.0235 mol) of trimethylsilyl iodide. The reaction mixture is stirred for 2 hours, then washed successively with cold 10% $Na_2S_2O_3$ solution, saturated $NaHCO_3$ solution, and brine, dried over $Na_2SO_4$, and concentrated in vacuo. The multicomponent residue is purified by high performance liquid chromatography (2:98/EtOAc:$CH_2Cl_2$) to afford 3.62 g (40%) of title compound: IR (KBr) 3280, 1785, 1715, 1675, 1520, 1365, 1300, 1150, and 1035 cm$^{-1}$; NMR (CDCl$_3$) 7.34 (s, 15H), 6.94–6.86 (m, 1H), 6.76 (s, 1H), 5.96–5.88 (m, 1H), 5.06 (d, 1H), 4.45 (d, 1H), 4.32 (d, 1H), 4.12 (s, 3H), 3.76 (d, 1H), 3.52 (d, 1H), 2.06 (s, 3H), and 1.56 (s, 9H).

PREPARATION OF STARTING A SUBSTITUENT-CONTAINING INTERMEDIATES

IA. 4-Cyano-2H,6H-1,2,6-thiadiazin-3-one 1,1-dioxide

A potassium alkoxide solution is prepared by adding 0.78 g (0.02 mole) of potassium to 10 ml of 2-propanol and diluting the solution with 10 ml of methanol. After the solution has cooled, 0.96 g (0.01 mole) of sulfamide in 10 ml of methanol are added dropwise with stirring to give a white suspension. Ethyl ethoxymethylenecyanocetate (1.69 g 0.01 mole) is added, dropwise, with stirring, and the resulting suspension is refluxed gently and stirred for 10 hours. After cooling, the solid is filtered and dissolved in water, and treated with acetic acid. The monopotassium salt thus obtained, is filtered off, dissolved in water and acidified with hydrochloric acid to give free title compound (35%), m.p. 209°–210° (nitromethane); uv λ max (water): 290 nm (ε 11,000); $^1$H(DMSO-d$_6$, δ): 9.25 (s, 2H, NH), 7.84 (s, 1H, H-5); ir (nujol, ν): 2250 cm$^{-1}$ (CN), 1650 cm$^{-1}$ (C=O).

Analysis for: C$_4$H$_3$N$_3$O$_3$S: Calculated: C, 27.75; H, 1.74; N, 24.27; Found: C, 27.68; H, 1.95; N, 24.51.

B. Monopotassium salt of IA

This compound has m.p. 250°–251° dec. (water); $^1$H nmr (DMSO-d$_6$, δ): 7.68 (s, 1H, H-5); ir (nujol, ν): 3500 cm$^{-1}$ (OH), 2240 cm$^{-1}$ (CN).

Analysis for: C$_4$H$_3$N$_3$O$_3$SK.H$_2$O: Calculated: C, 20.86; H, 2.17; N, 18.26; Found: C, 21.15; H, 2.08; N, 18.40.

II. 1H-2,1,3-Benzothiadiazin-4(3H)-one 2,2-dioxide

A 4.0 g (0.026 mole) sample of methyl anthranilate is dissolved in 10 ml of benzene and added rapidly to a stirred solution of 1.5 g (0.013 mole) of sulfamoyl chloride in 10 ml of benzene at 10°. A gum forms immediately, and after 2 minutes, 20 ml of 6N sodium hydroxide is added. The aqueous layer that forms is separated and acidified with concentrated hydrochloric acid. Upon cooling the mixture, a white crystalline solid precipitates and is filtered off. The crude yield is 2.0 g (66%). The product is completely soluble in sodium bicarbonate.

A small amount of the product is purified by dissolving in base and reprecipitating with acid; m.p. 228°–230°. In the infrared bands at 5.9 (carbonyl), 7.5 and 8.6μ (sulfonamide) are observed.

Analysis for: C$_7$H$_6$N$_2$SO$_3$: Calculated: C, 42.5; H, 3.02; N, 14.1; S, 16.2; Found: C, 42.6; H, 3.32; N, 14.0; S, 16.5.

An alternative synthesis is accomplished by using anthranilazide in place of the ester under the same reaction conditions.

Or thirdly, a sample of 0.20 g (0.00093 mole) of N-sulfamoylanthranilamide is dissolved in 5 ml of 1N sodium hydroxide and heated on the steam-bath for 4.5 hours. Ammonia is evolved during this period. After cooling the solution and acidifying it, 0.10 g (55%) of off-white fibers precipitate, m.p. 218°. The infrared spectrum of the product is identical with that of an authentic sample of 1H-2,1,3-benzothiadiazin-4(3H)-one-2,2-dioxide.

EXAMPLE 1

(6R,7R)-7-[[(Z)-(2-Amino-4-thiazolyl)(methoxyimino)-acetyl]amino]-3-[(4-cyano-3,6-dihydro-3-oxo-2H-1,2,6-thiadiazin-2-yl)methyl]-8-oxo-5-thia-1-azabicyclo[4.2.0]oct-2-ene-2-carboxylic acid S$^3$, S$^3$-dioxide

A.

(6R,7R)-3-[(4-Cyano-3,6-dihydro-3-oxo-2H-1,2,6-thiadiazin-2-yl)methyl]-7-[[(Z)-(methoxyimino)[2-[(triphenylmethyl)amino]-4-thiazolyl]acetyl]-amino]-8-oxo-5-thia-1-azabicyclo[4.2.0]oct-2-ene-2-carboxylic acid 1,1-dimethylethyl ester, S$^3$,S$^3$-dioxide A solution of 500 mg (0.61 mmol) of (6R,7R)-3-(iodomethyl)-7-[[(Z)-(methoxyimino)[4-[(triphenylmethyl)amino]-2-thiazolyl]acetyl]amino]-8-oxo-5-thia-1-azabicyclo[4.2.0]oct-2-ene-2-carboxylic acid 1,1-dimethylethyl ester, 129 mg of the monopotassium salt of 4-cyano-2H,6H-1,2,6-thiadiazin-3-one 1,1-dioxide, and 2 ml of dimethylformamide is stirred at ambient temperature under a nitrogen atmosphere for three hours. The reaction mixture is diluted with water, the resulting precipitate is collected, dissolved in ethyl acetate and washed with water. The organic phase is dried over Na$_2$SO$_4$ and concentrated under reduced pressure to give a waxy solid. Trituration with ether furnishes 265 mg (50%) of the title compound as a tan solid: IR (KBr) 3360 (br), 2210, 1785, 1720, 1670, 1610, 1520, 1370, 1300, 1150, and 1040 cm$^{-1}$. NMR (DMSO-d$_6$) δ 9.62–9.54 (m, 1H, exchangeable), 8.86–8.80 (m, 1H, exchangeable), 7.82 (s, 1H), 7.40–7.16 (m, 15H), 6.70 (s, 1H), 6.44 (s, 1H, exchangeable), 5.80–5.70 (m, 1H), 5.18–5.08 (m, 1H), 4.68 (d, 1H), 4.26 (d, 1H), 3.82 (s, 3H), 3.58–3.36 (m, 2H, partially obscured by H$_2$O), and 1.46 (s, 9H).

B.

(6R,7R)-7-[[(Z)-(2-Amino-4-thiazolyl)(methoxyimino)acetyl]amino]-3-[(4-cyano-3,6-dihydro-3-oxo-2H-1,2,6-thiadiazin-2-yl)methyl]-8-oxo-5-thia-1-azabicyclo[4.2.0]oct-2-ene-2-carboxylic acid 1,1-dimethylethyl ester S$^3$, S$^3$-dioxide A solution of 235 mg (0.27 mmol) of A. above and 2 ml of HCOOH (88%) is stirred at ambient temperature for two hours. The resulting precipitate is discarded. The filtrate is concentrated in vacuo to give a waxy solid. Trituration with ether affords 140 mg (83%) of the title compound as a tan powder: IR (KBr) 3300 (br), 2220, 1775, 1715, 1640, 1530, 1370, 1150, and 1040 cm$^{-1}$; NMR (DMSO-d$_6$) δ 9.72–9.62 (m, 1H, exchangeable), 7.86 (s, 1H), 6.78 (s, 1H), 6.48 (s, 1H, exchangeable), 5.92–5.78 (m, 1H), 5.28–5.14 (m, 1H), 4.80–4.64 (m, 1H), 4.36–4.20 (m, 1H), 3.88 (s, 1H), 3.58–3.36 (m, 2H, partially obscured by H$_2$O), and 1.5 (s, 9H).

C.

(6R,7R)-7-[[(Z)-(2-Amino-4-thiazolyl)(methoxyimino)acetyl]amino]-3-[(4-cyano-3,6-dihydro-3-oxo-2H-1,2,6-thiadiazin-2-yl)methyl]-8-oxo-5-thia-1-azabicyclo[4.2.0]oct-2-ene-2-carboxylic acid, S$^3$, S$^3$-dioxide, trifluoroacetate salt A solution of 110 mg (0.18 mmol) of B. above, 0.3 ml of anisole, and 2.5 ml of CF$_3$COOH is stirred at 0° C. for three hours. The volatiles are removed under high vacuum to give an oil. Trituration with ether furnishes 92 mg (92%) of the title compound as a yellow solid: IR (KBr) 3380 (br), 2220, 1780, 1670 (br), 1537, 1300, 1200, 1180, 1145, and 1040 cm$^{-1}$; NMR DMSO-d$_6$) δ 9.82–9.64 (m, 1H, exchangeable), 7.94 (s, 1H), 6.84 (s, 1H), 5.90–5.66 (m, 1H), 5.26–5.14 (m, 1H), 4.86–4.70 (m, 1H), 4.46–4.32 (m, 1H), 3.90 (s, 3H), and 3.68–3.48 (m, 2H).

EXAMPLE 2

(6R,7R)-7-[[(Z)-(2-Amino-4-thiazolyl)(methoxyimino)acetyl]amino]-3-[(1,4-dihydro-4-oxo-3H-2,1,3-benzothiadiazin-3-yl)methyl]-8-oxo-5-thia-1-azabicyclo[4.2.0]oct-2-ene-2-carboxylic acid, $S^3$, $S^3$-dioxide

A.

(6R,7R)-3-[(1,4-dihydro-4-oxo-3H-2,1,3-benzothiadiazin-3-yl)methyl]-7-[[(Z)-(methoxyimino)[2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester, $S^3$, $S^3$-dioxide To a mixture of 23 mg (0.57 mmol) of NaH (60% oil dispersion) and 1 ml of dimethylformamide at ambient temperature is added portionwise a solution of 96 mg (0.51 mmol) of 1H-2,1,3-benzothiadiazin-4(3H)-one 2,2-dioxide and 2 ml of dimethylformamide (gas evolution). After 20 minutes, a solution of 400 mg (0.49 mmol) of (6R,7R)-3-(iodomethyl)-7-[[(Z)-(methoxyimino)[4-[(triphenylmethyl)amino]-2-thiazolyl]acetyl]amino]-8-oxo-5-thia-1-azabicyclo[4.2.0]oct-2-ene-2-carboxylic acid 1,1-dimethylethyl ester and 3 ml of dimethylformamide is added portionwise. The reaction mixture is stirred at this temperature for four hours, diluted with ethyl acetate, and washed copiously with water, then brine. The organic phase is dried over $Na_2SO_4$, and concentrated in vacuo to give an oily solid. Trituration with ether provides 345 mg (79%) of the title compound, a light brown solid: IR (KBr) 3400 (br), 3260 (br), 1785, 1715, 1660, 1530, 1370, 1290, 1255, 1150, and 1040 cm$^{-1}$; NMR DMSO-$d_6$) δ 9.56 (d, 1H, exchangeable), 8.90–8.80 (m, 1H, exchangeable), 7.96–7.90 (m, 1H), 7.44–7.22 (m, 16H), 7.04–6.96 (m, 1H), 6.88–6.80 (m, 1H), 6.72 (s, 1H), 5.72–5.64 (m, 1H), 5.12 (d, 1H), 4.84 (d, 1H), 4.66 (d, 1H), 3.82 (s, 3H), 3.56–3.26 (m, 2H), partially obscured by $H_2O$), and 1.55 (s, 9H).

B.

(6R,7R)-7-[[(Z)-(2-Amino-4-thiazolyl)(methoxyimino)acetyl]amino]-3-[(1,4-dihydro-4-oxo-3H-2,1,3-benzothiadiazin-3-yl)methyl]-8-oxo-5-thia-1-azabicyclo[4.2.0]oct-2-ene-2-carboxylic acid 1,1-dimethylethyl ester, $S^3$, $S^3$-dioxide A solution of 300 mg (0.34 mmol) of A. above and 4 ml of HCOOH (88%) is stirred at ambient temperature for three hours. The resulting precipitate is discarded. The filtrate is concentrated in vacuo to give a waxy solid. Trituration with ether furnishes 187 mg (85%) of the title compound as a tan powder: IR (KBr) 3440 (br), 3300, 3200 (br), 1780, 1710, 1660 (br), 1620, 1520, 1450, 1365, 1210 (br), 1145, and 1030 cm$^{-1}$; NMR (DMSO-$d_6$) δ 9.60 (d, 1H, exchangeable), 7.96–7.88 (m, 1H), 7.46–7.32 (m, 1H), 7.02–6.94 (m, 1H), 6.86–6.80 (m, 1H), 6.74 (s, 1H), 5.82–5.74 (m, 1H), 5.14 (d, 1H), 4.84 (d, 1H), 4.66 (d, 1H), 3.84 (s, 3H), 3.42–3.26 (m, 2H, partially obscured by $H_2O$), and 1.54 (s, 9H).

C.

(6R,7R)-7-[[(Z)-(2-Amino-4-thiazolyl)(methoxyimino)acetyl]amino]-3-[(1,4-dihydro-4-oxo-3H-2,1,3-benzothiadiazin-3-yl)methyl]-8-oxo-5-thia-1-azabicyclo[4.2.0]oct-2-ene-2-carboxylic acid $S^3$, $S^3$-dioxide, trifluoroacetate salt A solution of 110 mg (0.17 mmol) of B. above, 0.4 ml of anisole, and 4 ml of $CF_3COOH$ is stirred at 0° C. for two hours. The volatiles are removed under high vacuum to give a brown oil. Trituration with ether provides 94 mg (93%) of the title compound as a tan powder: IR (KBr) 3280 (br), 3100 (br), 1780, 1670 (br), 1530 (br), 1360 (br), 1180, 1135, and 1040 cm$^{-1}$; NMR (DMSO-$d_6$) δ 9.66 (d, 1H, exchangeable), 8.08–7.96 (m, 1H), 7.36–7.20 (m, 1H), 7.00–6.94 (m, 1H), 6.86–6.76 (m, 1H), 6.80 (s, 1H), 5.84–5.74 (m, 1H), 5.16(d, 1H), 5.06–4.82 (m, 2H), and 3.54–3.32 (m, 2H, partially obscured by $H_2O$).

EXAMPLE 3

The compounds of the invention are tested for their antibacterial activity. The test can be carried out in two ways:

A. The organisms used in the test comprise the following: *Staphylococcus aureus* (penicillin-sensitive and resistant), *Pseudomonas aeruginosa, Escherichia coli, Salmonella pneumoniae, Bordetella bronchiseptica, Proteus vulgaris, P. mirabilis, Acinetobacter calcoaceticus.*

Test organisms may be added or deleted in order to reflect current clinical patterns of antibiotic susceptibility or shifts in pathogenic potential.

Stock solution of appropriate medium (e.g. Mueller-Hinton Broth) is sterilized. Starting at a predetermined concentration (e.g. 250 µg/ml), two-fold dilutions are made with the Dynatech Automatic Diluter in a Microtiter plate of 8 rows of 12 wells each in which 11 wells in each row contain 50 µl of medium (e.g. Mueller-Hinton Broth) and the 12th well contains in 100 µl an aliquot of the compound to be tested. The diluted plates are inoculated using the Dynatech Automatic Inoculator which delivers the final inoculum (e.g. 10$^5$ cfu/ml of a seven-hour culture which has been incubated at 35° C.).

Plates are sealed with tape and incubated (e.g. 18 hours at 35° C.).

The Minimal Inhibitory Concentration (MIC) in µg/ml is determined; this is the least concentration that completely inhibits the test organism as observed visually.

B. The organisms used in the test comprise the following: *Staphylococcus aureus* (penicillin-sensitive and resistant), *Pseudomonas aeruginosa, Escherichia coli, Salmonella pneumoniae, Bordetella bronchiseptica, Proteus vulgaris, P. mirabilis, Acinetobacter calcoaceticus.*

Test organisms may be added or deleted in order to reflect current clinical patterns of antibiotic susceptibility or shifts in pathogenic potential.

Organisms are normally grown for 18 hours in Brain Heart Infusion at 35° C. Cultures are adjusted with saline to MacFarland No. 1.5 standard prior to use.

Stock concentrations (e.g. 2,5000 µg or units per ml) are prepared in a suitable vehicle. Two-fold dilutions are made. One ml quantities of each dilution are incorporated in 9 ml of the appropriate agar (e.g. Seed) in sterile Petri plates. The hardened surface is inoculated with test organisms by use of a Steers replicating device. The plates are incubated (e.g. 18 hours at 35° C.) and activity is determined.

The least amount of material that completely inhibits the test organisms is the Minimal Inhibitory Concentration (MIC), which is expressed in µg or units per ml.

The compound of the invention, when tested according to the above outlined procedures, give the results summarized in Table 1.

TABLE 1

| Organism | Compound of Example No. MIC (μg/ml) | | | |
|---|---|---|---|---|
| | 1 B.[b] | 1 C.[b] | 2 B.[a] | 2 C.[a] |
| *Staphylococcus aureus* ATCC 29213 | 64 | 32 | 64 | 32 |
| *Streptococcus faecalis* ATCC 29212 | 256 | 128 | 128 | 128 |
| *Enterobacter cloacae* ATCC 13047 | 64 | 32 | 64 | 64 |
| *Escherichia coli* ATCC 25922 | 2 | 1 | 8 | 4 |
| *Klebsiella pneunomiae* KL-1 | 1 | 0.125 | 4 | 2 |
| *Proteus vulgaris* A 84354 1 | 0.25 | 1 | 1 | 0.25 |
| *Pseudomonas aeruginosa* ATCC 27853 | 256 | 256 | 128 | 128 |
| *Serratia marcescens* ATCC 13880 | 32 | 8 | 64 | 16 |

[a] = compound tested according to procedure A outlined above.
[b] = compound tested according to procedure B outlined above.

The results show the compounds of the invention to have antibacterial activity against the organisms used in the test procedures, in particular against Gram-negative organisms.

What is claimed is:

1. A compound having the formula

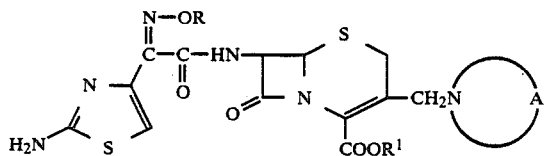

wherein

R is hydrogen, lower alkyl, lower alkenyl, lower alkynyl, cyclo lower alkyl, or phenyl;

R$^1$ is hydrogen, lower alkyl or an alkali metal cation;

A is

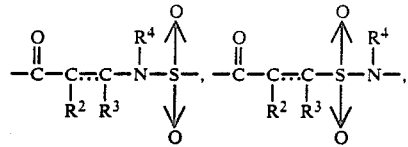

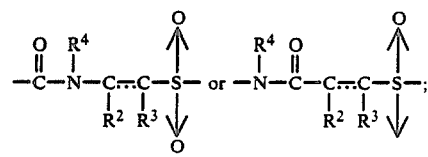

R$^2$ and R$^3$ are each individually hydrogen, lower alkyl, carboxy, lower alkoxycarbonyl, cyano, nitro, trifluoromethyl, phenyl or naphthyl; or R$^2$ and R$^3$ taken together represent

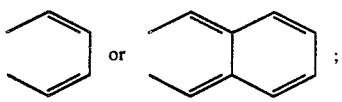

and the dotted line denotes an optional double bond; and

R$^4$ is hydrogen, lower alkyl, phenyl or naphthyl.

2. The compound of claim 1, having the name (6R,7R)-7-[[(Z)-(2-amino-4-thiazolyl)(methoxyimino)acetyl]amino]-3-[(4-cyano-3,6-dihydro-3-oxo-2H-1,2,6-thiadiazin-2-yl)methyl]-8-oxo-5-thia-1-azabicyclo[4.2.0]oct-2-ene-2-carboxylic acid 1,1-dimethylethyl ester S$^3$, S$^3$-dioxide.

3. The compound of claim 1, having the name (6R,7R)-7-[[(Z)-(2-amino-4-thiazolyl)(methoxyimino)acetyl]amino]-3-[(4-cyano-3,6-dihydro-3-oxo-2H-1,2,6-thiadiazin-2-yl)methyl]-8-oxo-5-thia-1-azabicyclo[4.2.0]oct-2-ene-2-carboxylic acid, S$^3$, S$^3$-dioxide.

4. The compound of claim 1, having the name (6R,7R)-7-[[(Z)-(2-amino-4-thiazolyl)(methoxyimino)acetyl]amino]-3-[(1,4-dihydro-4-oxo-3H-2,1,3-benzothiadiazin-3-yl)methyl]-8-oxo-5-thia-1-azabicyclo[4.2.0]oct-2-ene-2-carboxylic acid 1,1-dimethylethyl ester, S$^3$, S$^3$-dioxide.

5. The compound of claim 1, having the name (6R,7R)-7-[[(Z)-(2-amino-4-thiazolyl)(methoxyimino)acetyl]amino]-3-[(1,4-dihydro-4-oxo-3H-2,1,3-benzothiadiazin-3-yl)methyl]-8-oxo-5-thia-1-azabicyclo[4.2.0]oct-2-ene-2-carboxylic acid S$^3$, S$^3$-dioxide.

* * * * *